(12) United States Patent
Presswood, Jr. et al.

(10) Patent No.: US 11,359,253 B2
(45) Date of Patent: Jun. 14, 2022

(54) GASIFICATION OR LIQUEFACTION OF COAL USING A METAL REACTANT ALLOY COMPOSITION

(71) Applicants: Ronald G. Presswood, Jr., Houston, TX (US); Ian C. Bishop, Houston, TX (US)

(72) Inventors: Ronald G. Presswood, Jr., Houston, TX (US); Ian C. Bishop, Houston, TX (US)

(73) Assignee: Elemental Recycling, Inc., Houston, TX (US)

( * ) Notice: Subject to any disclaimer, the term of this patent is extended or adjusted under 35 U.S.C. 154(b) by 628 days.

(21) Appl. No.: 16/434,771

(22) Filed: Jun. 7, 2019

(65) Prior Publication Data
US 2019/0284651 A1    Sep. 19, 2019

Related U.S. Application Data

(63) Continuation of application No. 14/973,243, filed on Dec. 17, 2015, now Pat. No. 10,316,375, which is a
(Continued)

(51) Int. Cl.
*C01B 32/05* (2017.01)
*C10J 3/57* (2006.01)
(Continued)

(52) U.S. Cl.
CPC .......... *C21B 13/0006* (2013.01); *C01B 17/02* (2013.01); *C01B 17/033* (2013.01);
(Continued)

(58) Field of Classification Search
CPC .................... C10J 3/57; C10J 2300/093; C10J 2300/0969; C10J 2300/1675
See application file for complete search history.

(56) References Cited

U.S. PATENT DOCUMENTS

| 3,812,620 A | 5/1974 | Titus et al. | |
| 4,345,990 A * | 8/1982 | Fahlstrom | C10G 1/006 |
| | | | 201/11 |

(Continued)

FOREIGN PATENT DOCUMENTS

| CN | 1546614 A | 11/2004 |
| CN | 201273767 Y | 7/2009 |

(Continued)

OTHER PUBLICATIONS

Helmensteine, Todd, "Activity Series of Metals", About.com Chemistry. About.com, Dec. 22, 2010. Web. Jun. 11, 2014. http://chemistry.about.com/od/chartstables/a/Activity-Series-Of-Metals.htm.
(Continued)

*Primary Examiner* — Matthew J Merkling
(74) *Attorney, Agent, or Firm* — Frost Brown Todd LLC

(57) ABSTRACT

This invention relates to a method and apparatus for gasifying or liquifying coal. In particular, the method comprises reacting a coal with a molten aluminum or aluminum alloy bath. The apparatus includes a reaction vessel for carrying out the reaction, as well as other equipment necessary for capturing and removing the reaction products. Further, the process can be used to cogenerate electricity using the excess heat generated by the process.

13 Claims, 3 Drawing Sheets

Related U.S. Application Data continuation of application No. 13/487,430, filed on Jun. 4, 2012, now Pat. No. 9,216,905.

(60) Provisional application No. 61/493,247, filed on Jun. 3, 2011.

(51) Int. Cl.

| | | |
|---|---|---|
| *C01B 17/033* | (2006.01) | |
| *C01B 17/02* | (2006.01) | |
| *C21B 13/00* | (2006.01) | |
| *F27D 3/16* | (2006.01) | |
| *C07C 1/00* | (2006.01) | |
| *C22B 15/00* | (2006.01) | |
| *C22B 61/00* | (2006.01) | |

(52) U.S. Cl.
CPC ............... *C01B 32/05* (2017.08); *C07C 1/00* (2013.01); *C10J 3/57* (2013.01); *C22B 15/0052* (2013.01); *C22B 61/00* (2013.01); *F27D 3/16* (2013.01); *C10J 2300/093* (2013.01); *C10J 2300/0969* (2013.01); *C10J 2300/1675* (2013.01)

(56) References Cited

U.S. PATENT DOCUMENTS

| | | | | |
|---|---|---|---|---|
| 4,649,867 | A | | 3/1987 | Cordier et al. |
| 5,395,405 | A | * | 3/1995 | Nagel .................. C07C 1/00 48/197 R |
| 5,640,707 | A | | 6/1997 | Nagel et al. |
| 5,640,708 | A | | 6/1997 | Conochie et al. |
| 5,645,615 | A | * | 7/1997 | Malone ................ C10J 3/57 48/197 R |
| 5,765,489 | A | * | 6/1998 | Hugentobler ............. C21B 3/04 110/235 |
| 5,858,059 | A | | 1/1999 | Abramovich et al. |
| 6,264,722 | B1 | | 7/2001 | Kepplinger et al. |
| 6,322,745 | B1 | | 11/2001 | Leigh et al. |
| 6,685,754 | B2 | * | 2/2004 | Kindig .................... C01B 3/025 252/372 |
| 7,318,890 | B1 | | 1/2008 | Malone |
| 7,335,320 | B2 | | 2/2008 | Kindig |
| 7,875,090 | B2 | * | 1/2011 | Dietenberger ......... C10K 1/026 423/655 |
| 8,303,916 | B2 | * | 11/2012 | Collins ................... C01B 3/06 422/600 |
| 2006/0208400 | A1 | | 9/2006 | Schmeler |
| 2007/0183966 | A1 | | 8/2007 | Nakagawa et al. |
| 2009/0071289 | A1 | | 3/2009 | Fekete et al. |
| 2010/0283009 | A1 | | 11/2010 | Nickels et al. |
| 2013/0180363 | A1 | | 7/2013 | Nakamoto et al. |

FOREIGN PATENT DOCUMENTS

| | | |
|---|---|---|
| GB | 284722 A | 11/1928 |
| GB | 1528655 A | 10/1978 |

OTHER PUBLICATIONS

Derwent Acc-No. 2009-L89064 for patent family CN 201273767 Y by Li et al. published Jul. 15, 2009. Abstract.

CN 201273767 Y Machine translation, published Jul. 15, 2009 (downloaded from Google Patents).

CN 1546614 A Machine Translation (Year: 2004).

Yamaguchi, Katsunori et al. "Copper Enrichment of Iron-Base Alloy Scraps by Phase Separation in Liquid Fe—Cu—P and Fe—Cu—P—C Systems." Materials Transactions. vol. 47, No. 7, p. 1864-1868. (Year: 2006).

\* cited by examiner

GASIFICATION OR LIQUEFACTION OF COAL USING A METAL REACTANT ALLOY COMPOSITION

CROSS REFERENCE TO RELATED INFORMATION

This application is a continuation of U.S. patent application Ser. No. 14/973,243, now U.S. Pat. No. 10,316,375, titled, "Gasification or Liquefaction of Coal Using a Metal Reactant Alloy Composition", filed Dec. 17, 2015; which is a continuation of U.S. patent application Ser. No. 13/487,430, now U.S. Pat. No. 9,216,905, titled, "Gasification or Liquefaction of Coal Using a Metal Reactant Alloy Composition", filed Jun. 4, 2012; which claims the benefit of U.S. Provisional Patent Application No. 61/493,247, filed Jun. 3, 2011, titled, "Gasification or Liquefaction of Coal Using a Metal Reactant Alloy Composition", the contents of which are hereby incorporated herein in its entirety.

TECHNICAL FIELD

The present invention relates to a method to gasify or liquefy coal and to capture and recover carbon, sulfur, hydrocarbons, and heavy metals from the coal using a molten aluminum or alloy bath composed of aluminum or an aluminum alloy that includes, but is not limited to zinc, iron, copper, silicon and calcium alloys.

BACKGROUND OF THE INVENTION

Although a number of methods exist to gasify or liquefy coal, these methods are costly and in some cases create a secondary waste that can be more of a problem than the actual gas stream itself. Currently, coal gasification or liquefaction methods create greenhouse gases such as carbon monoxide carbon dioxide, as well as, other bi-products such as tar, ammonia, and tar-water emulsions. Further, these processes also produce slag, which currently must be land filled and there is currently no efficient method to recovery heavy metals, such as mercury, that typically are found in coal. While these processes work, they require significant energy input or create waste streams that must be disposed of at a cost to the operator and with potential future environmental impact. Thus, there is a need in the art for an improved method to economically gasify or liquefy coal while recovering the remaining carbon, sulfur and any heavy metals.

BRIEF SUMMARY OF THE INVENTION

The present invention provides an apparatus for gasifying or liquefying coal. The coal can be any coal from peat (a coal precursor) to lignite (60% carbon) to anthracite (90+% carbon). The process utilizes a molten aluminum or molten aluminum alloy bath. The aluminum can be alloyed with metals that include, but are not limited to zinc, iron, copper, silicon, and calcium. The coal is ground and can be dried, and then the powder is introduced into the bath below the surface. The powdered coal is forced below the surface using an inert gas such as Nitrogen or argon. In the process excess heat is generated and can be used to facilitate other processes such as cogeneration of power. As the coal is passed through the bath, the aluminum or aluminum alloy bath reacts with the coal to break it down to its elemental parts. These elements are then removed from the bath using a gravimetric process and a gas capture process. The elements removed from the bath can include, but are not limited to, carbon, sulfur, hydrogen, nitrogen, mercury, copper, iron, as well as other heavy metals. The process can also produce methane and other hydrocarbons. The elemental materials can be recovered and sold and the hydrocarbons are recovered and sold or burned to facilitate the process. The inert gas is reprocessed and reused.

The aluminum or aluminum alloy bath is able to remove oxygen compounds by chemically reacting with them at high temperature. This allows the carbon bonds of the coal to be broken, producing volatile organic compounds, as well as elemental compounds.

This process has been evaluated in laboratory tests using ground lignite coal. The ground coal was passed through molten aluminum. The flue gas produced and the final alloy mass were analyzed using scanning electron microscope. (See Table 1).

TABLE 1

Process Mass Analysis

| | MOL % |
|---|---|
| $H_2$ | 25.181 |
| $CO_2$ | 27.345 |
| CO | 14.265 |
| C | 19.898 |
| C2 | 2.824 |
| C2 | 2.999 |
| C3 | 0.939 |
| C3 | 2.228 |
| C4 | 0.199 |
| C4 | 1.034 |
| C4 | 0.000 |
| C5 | 0.199 |
| C6 and above | 2.888 |
| | 100 |

FIG. 1 shows the basic process flow. In the basic process, powdered coal is introduced below the surface of the molten metal bath 103 using an injection feed system 101 through feed line 102. The elemental material, such as carbon, sulfur and the like, is captured 104, less dense secondary compounds are removed from the surface of bath 105, and denser secondary compounds are removed from the bottom of the bath 106. While this has been described as a method to gasify or liquefy coal, use of this method to other organic compounds, such as, for example, peat, wood, and grass are also contemplated.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which.

DETAILED DESCRIPTION OF THE INVENTION

The present invention provides a process to gasify or liquefy coal. The process utilizes a molten aluminum or molten aluminum alloy bath. The process utilizes a molten aluminum bath as the reactant. The coal, which is introduced below the surface of the molten aluminum bath, reacts with the aluminum to decompose the coal. In the process, elemental carbon, sulfur, copper, iron, and heavy metals and molecular hydrogen, nitrogen, methane, and other hydrocarbons are removed from the molten bath. The products can be sold and the nitrogen is either vented to the atmosphere or captured.

The process utilizes a molten metal as the primary reactant. In the preferred embodiments the molten metal is aluminum or an aluminum bath. The aluminum can also be alloyed with other elements including, but not limited to, zinc, iron, copper, silicon, magnesium, and calcium. Other metals and metal alloys such as calcium and silicon are also envisioned. The flue gas stream, which contains oxygen containing greenhouse gases produced by combustion processes, is passed through the aluminum alloy bath to remove the oxygen-containing gases from the flue gas stream.

In the process, excess heat is generated and can be used to facilitate other processes such as cogeneration of power. The excess generated by the process is a function of the makeup of the greenhouse gases in the flue gas feed.

When the coal contains other compounds, those compounds can also be decomposed or captured. For example, if the coal contains inorganic compounds, such as chlorine, the process will produce an aluminum salt, in this case aluminum chloride. The present invention also provides a method and apparatus for capturing heavy metals, such as, but not limited to mercury, which is often found in coal. In the process, the molten metal bath breaks down the metal compounds as they are introduced into the molten metal bath. As additional aluminum is added to the bath, the heavy metals settle to the bottom of the reaction vessels and are removed from the reaction vessel. While some aluminum may be entrained in the heavy metals that are removed from the bottom of the reaction vessel, the aluminum can be removed and refined and the heavy metals can be captured.

Figure 1:
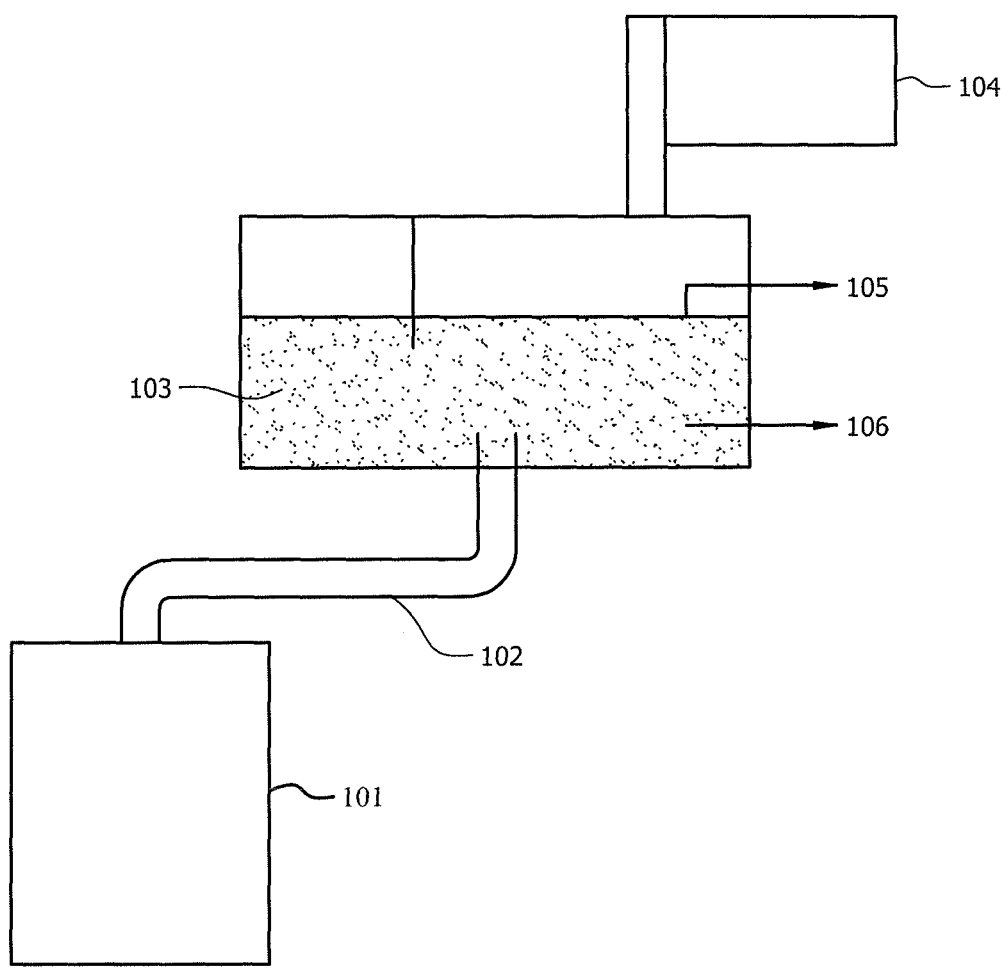
FIG. 1 shows the basic process flow.
Figure 2:
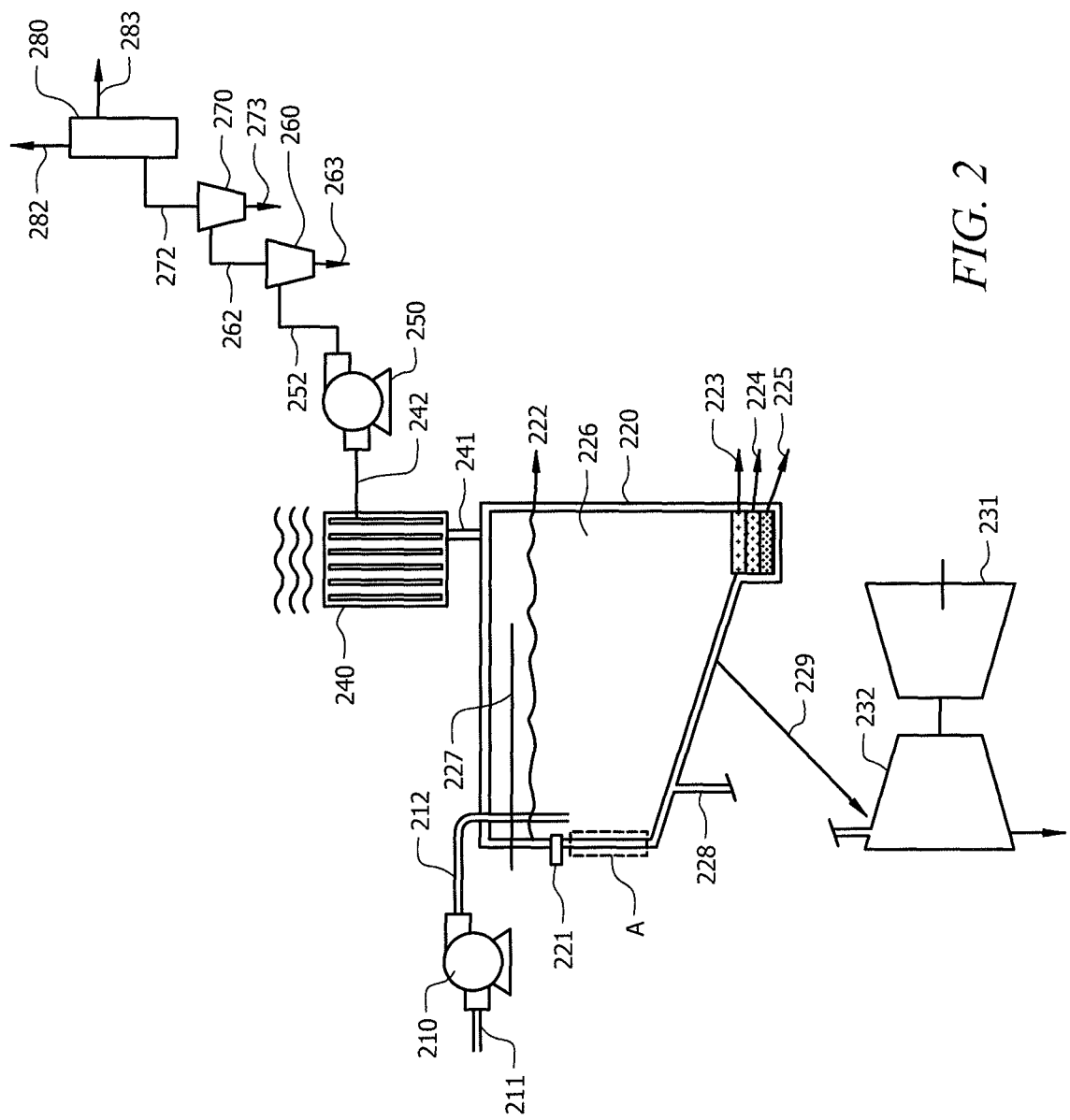
FIG. 2 shows a typical process flow.

A detailed process flow is shown in FIG. 2. While the process described discusses processing coal, other organic materials can be processed using the invention. The ground coal is introduced into the treatment process through blower feed line 211. Blower 210 is used to inject the ground coal into reaction vessel 220 through injection line 212. Injection line 212 introduces the ground coal stream, which is entrained in an inert gas such as nitrogen, below the surface 222 of the molten aluminum compound 226. Injection line 212 must be sufficiently below the surface 222 of the molten aluminum compound 226 to allow for sufficient mixing. The heavy products of the reaction, typically the heavy metals described above will settle out in the reaction vessel. The reaction vessel typically has a sloped bottom, however other designs such conical and the like can be utilized. Once the heavy products settle out, they are collected using collection lines 223, 224, and 225. Collection lines 223, 224, and 225 allow for heavy metals of different densities to be removed. Depending on the size of the process, the heavy products can be continuously removed or a batch removal process can be used.

Reaction vessel 220 also includes an aluminum feed line 221, which is used to supply additional aluminum compound to replace that consumed by the reaction with the ground coal. Additional heat may be required during start-up, for example. Heater 227 is provided for this purpose. Heater 227 can be any type heater, including radiative, inductive, and convective. For example, heater 227 would be a microwave heater or a radio frequency heater wherein the frequency is tuned for the metal alloy used.

Figure 3:
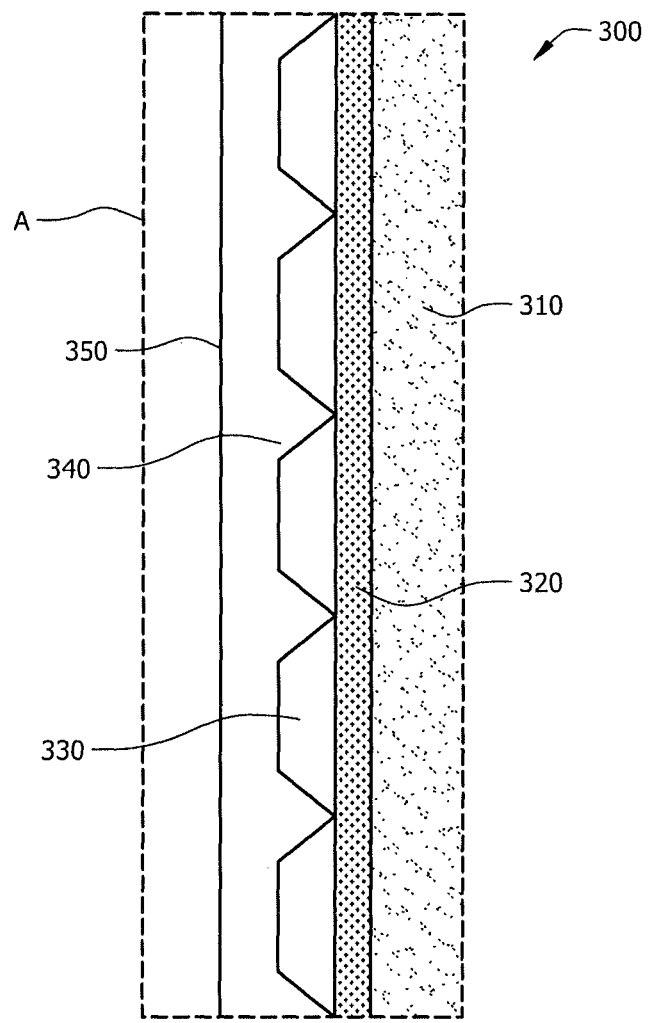
FIG. 3. shows a detailed cross sectional view of the reaction vessel wall.

Thus, the heat generated by the process must be removed. Section A, which is shown in more detail in FIG. 3 shows one way the heat can be removed from the process. The reaction vessel 220 is lined with a refractory material 310, which protects the vessel wall 320. Cooling plate 330 is attached to the vessel wall 320 and cooling water is circulated in the channels created between the cooling plant 330 and the vessel wall 320. Insulation 340 surrounds the cooling plate to maximize heat recovery, as well as for safety purposes. Once the cooling water picks up the heat generated from the process, it can be either sent to a cooling tower or the heat can be recovered and used for other purposes. If the process is used in a facility that needs a hot water source, then the heat recovery system can be designed for this purpose. However, the heat can also be used to generate electricity.

Turning back to FIG. 2, a steam turbine electric generation process is represented. In this case, the cooling water is introduced thorough cooling feed 228. As the cooling water travels around the reaction vessel 220, it picks up heat and steam is generated. The steam generated is then sent via steam line 229 to steam turbine 232. The steam passes through the turbine and as it condenses, turns the turbine blades of turbine 232. Turbine 232 is coupled to generator 231. As the turbine turns the rotor of generator 231 though the stator, it generates electricity. While this process is only briefly described, this steam turbine-electric generator process is well known in the art. And any steam turbine-electric generator process could be utilized.

Also, as described above, the reaction will also produce elemental carbon, elemental sulfur, molecular nitrogen and molecular hydrogen. These will be removed from the reaction vessel using blower 250. Blower 250 will pull high temperature elemental carbon, elemental sulfur, molecular nitrogen and molecular hydrogen from the reaction vessel 220 through heat exchanger feed line 241 into heat exchanger 240. Heat exchanger 240 will then cool this material to enable further processing. Any hydrocarbons that are produced may also be condensed in heat exchanger 240. These liquid hydrocarbons can be collected for further use or sale. Heat exchanger 240 can be any heat exchanger, however in the preferred embodiment, heat exchanger 240 is a forced air heat exchanger, however other heat exchangers, are also envisioned. The process steam then leaves the heat exchanger through line 242 and passes through blower 250 and blower discharge line 252 into two cyclone separators. The first separator 260 separates out carbon from process stream. The carbon is collected though separation line 263. The remaining process stream through line 262 proceeds to the second separator 270, which separates out sulfur from the process stream. The sulfur is collected through separation line 273. The remaining process stream, which may include gaseous nitrogen and hydrogen, is then sent through line 272 and separated in cryo unit 280. In this unit, the gas stream is cooled further and to allow the components to be separated into different components that are sent through lines 282 and 283.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A device for producing liquefied products from solid coal particles, the device comprising:
    a reaction vessel designed to hold a molten metal;
    a metal feed line designed to introduce metal into the reaction vessel;
    a coal injection line having an outlet in the reaction vessel, the outlet positioned such that coal introduced into the reaction vessel enters the molten metal below an upper surface of the molten metal such that the coal is mixed into the molten metal and reacts with the molten metal to produce a liquefied product;
    wherein the liquefied product separates by settling from the molten metal within the reaction vessel;
    a first collection line attached to a lower portion of the reaction vessel;
    a second collection line attached to the reaction vessel, wherein the first collection line and the second collection line are designed to remove components of differing densities of the liquified product from the reaction vessel;
    a separator feed line designed to remove reaction gas from an upper portion of the reaction vessel; and
    a separator designed to remove particulate matter from the reaction gas.

2. The device of claim 1, wherein the reaction vessel comprises a reaction vessel wall, a refractory material, and a cooling plate, wherein the cooling plate forms a channel for a cooling fluid between the cooling plate and the reaction vessel wall.

3. The device of claim 1, wherein the molten metal comprises aluminum.

4. The device of claim 1, wherein the molten metal comprises aluminum alloy.

5. The device of claim 1, wherein the molten metal comprises at least one alloy material selected from the group consisting of silicon, magnesium, zinc, copper, iron, and calcium.

6. The device of claim 1, wherein the molten metal is silicon.

7. The device of claim 1, wherein the molten metal is silicon alloy.

8. The device of claim 1, wherein molten metal consumed by reaction in the reaction vessel is replace by adding metal through the metal feed line.

9. The device of claim 1, wherein the separator is a heat exchanger designed produce gasified and/or liquefied products from the reaction gas.

10. The device of claim 1, wherein the liquefied product is comprised of two or more components of different densities.

11. A device for producing liquefied products from solid coal particles, the device comprising:
    a reaction vessel holding molten aluminum;
    an aluminum feed line connecting an aluminum feed source to the reaction vessel;
    a coal injection line connecting a coal feed source and having an outlet in the reaction vessel, the outlet positioned to introduce coal into the reaction vessel below an upper surface of the molten aluminum thereby mixing the coal into the molten aluminum such that the coal reacts with the molten aluminum to produce a liquefied product, wherein the liquefied product separates from the molten aluminum by settling to a bottom of the reaction vessel;
    a first collection line and a second collection line each attached to a lower portion of the reaction vessel and designed to remove the liquefied product from the reaction vessel, wherein a first component of a lighter density is removed using the first collection line, and a second component of a heavier density is removed using the second collection line;
    a heat exchanger feed line designed to remove reaction gas from an upper portion of the reaction vessel; and
    a heat exchanger receiving the reaction gas from the heat exchanger feed line and removing particulate matter from the reaction gas.

12. The device of claim 11, wherein the reaction vessel comprises a reaction vessel wall, a refractory material, and a cooling plate, wherein the cooling plate forms a channel for a cooling fluid between the cooling plate and the reaction vessel wall.

13. The device of claim 11, wherein the molten aluminum comprises an aluminum alloy.

* * * * *